United States Patent [19]

Goldman

[11] Patent Number: 4,840,272

[45] Date of Patent: Jun. 20, 1989

[54] CONTAINER FOR INJECTION NEEDLES WITH SAFETY APPARATUS

[76] Inventor: Michael C. Goldman, 7801 Connecticut Ave., Chevy Chase, Md. 20815

[21] Appl. No.: 236,606

[22] Filed: Aug. 25, 1988

[51] Int. Cl.$^4$ .......................... A61M 5/32; B65D 85/20
[52] U.S. Cl. .................................... 206/365; 604/192; 604/263
[58] Field of Search ................ 206/364, 365; 604/192, 604/263

[56] References Cited

U.S. PATENT DOCUMENTS

| | | | |
|---|---|---|---|
| 1,007,804 | 11/1911 | Schimmel | 206/365 X |
| 4,106,621 | 8/1978 | Sorenson | 206/365 |
| 4,643,722 | 2/1987 | Smith, Jr. | 206/365 X |

FOREIGN PATENT DOCUMENTS

| | | | |
|---|---|---|---|
| 365380 | 12/1922 | Fed. Rep. of Germany | 206/365 |
| 1574983 | 9/1980 | United Kingdom | 206/365 |

*Primary Examiner*—William Price
*Attorney, Agent, or Firm*—John J. Byrne

[57] ABSTRACT

A container for injection needles of the type used with a syringe having a needle casing and a closure cap with an aperture through which slidably receives a member extending longitudinally outwardly from said casing, the distal end of said member having a grasping surface whereby the casing is supportable by one hand of the syringe user as the needle is re-inserted into the container after use with the other hand, the continued effect of which is to cause both hands to be rearwardly of the needle during re-insertion.

4 Claims, 3 Drawing Sheets

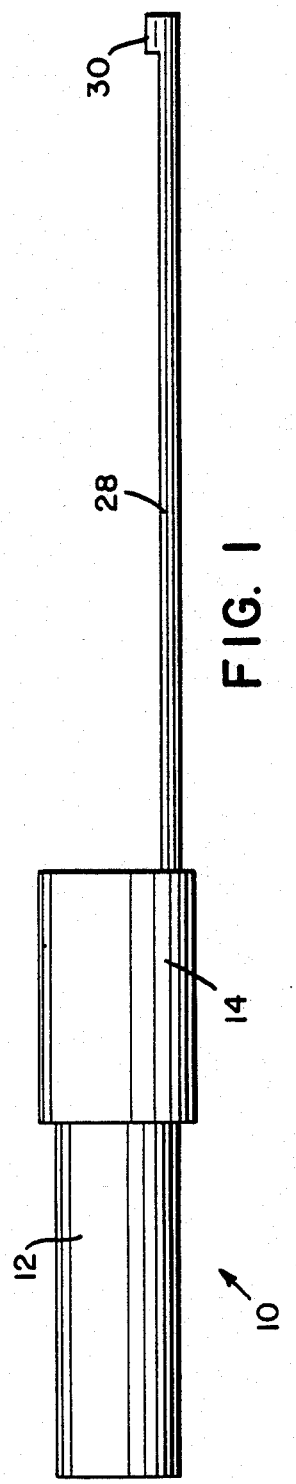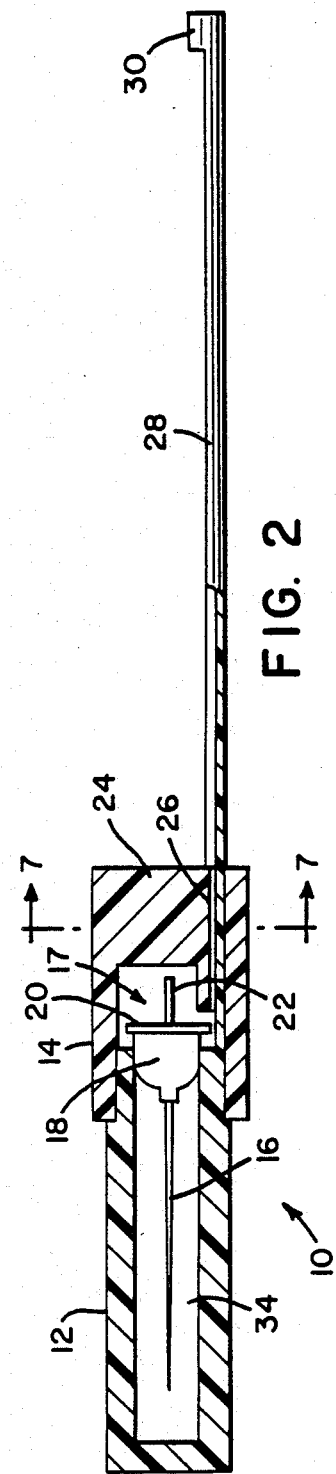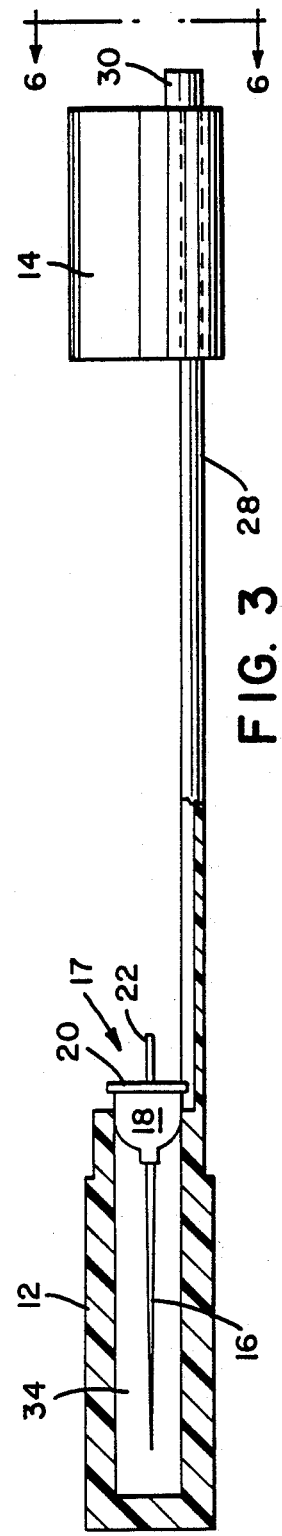

CONTAINER FOR INJECTION NEEDLES WITH SAFETY APPARATUS

BACKGROUND AND FIELD OF THE INVENTION

In the routine use of injection needles of syringes by medical, dental, veterinary, research, laboratory and industrial personnel, it is not uncommon for accidental puncture wounds to be reported either as self-inflicted while replacing the needle in its container or by someone handling trash containing used needles that have been discarded without a protective cap. Many times, the accident results in a minor injury of no significance other than discomfort. However, with increased concern over AIDS, hepatitis and other serious contagious diseases, a seemingly innocuous, shallow needle-stick can become a potentially fatal accident.

Many designs of the containers currently in use in the packaging of injection needles can contribute to potential accidents. In fact, the likelihood of accidental needle-sticks occurring by virtue of the fact that when a needle has been used and the user attempts to recap the working end of the needle, one holds the plastic or rubber needle cap (cover or sheath) in front of the point of the needle and attempts to insert the tip of the needle. If one misses the cap orifice or is bumped in the process, it is possible that the user will be stuck in the fingers holding the needle cap.

For persons who must handle hypodermic needles, puncturing of the fingers presents a serious concern. The pricking is most apt to occur in the act of replacing the cover. (However, covers must be replaced, even for disposable needles, for it is hazardous to discard a used needle into the trash with an exposed needle.)

When the needles are re-covered, it is usually after they have been removed from a patient and contaminated with the patient's microorganisms. The covers present a small target when held in one's hand, and if this target is missed by the syringe needle, a dangerous skin breaking by the contaminated needle can occur.

SUMMARY OF THE INVENTION

Described is a type of needle commonly used in dentistry. This needle differs from several other types of needles in that they have—in addition to the front sharp-pointed working end—a rear shorter extension projecting from a screw-on hub. After use, this rear projecting needle extension also has the potential for accidental "needle sticks" if it is not covered by the end cap. While other configurations which lack the rear needle extensions cannot so easily cause puncture-type accidents, the rear end of a used needle is still, however, contaminated and potentially dangerous if only to a lesser degree and, therefore, should be protectively covered following use and prior to disposal.

Therefore, a principal objective of this invention is to provide a syringe container which houses a syringe needle from which the needle can be readily removed and inserted and, in turn, re-inserted into the container with relatively little risk to the user.

Another objective of this invention is to provide a syringe needle container in which the casing has an outward extension that is slidably received by the casing cap or cover. The extension is dimensioned so that the cap will remain connected to the casing and wherein the cap can slide over the casing so that the contaminated needle can be easily re-covered.

A still further objective of this invention is to provide a hypodermic syringe needle container which is simple in construction, safe in use and which does not materially add to the cost thereof.

Another objective of the invention is to provide a container of a type which does not materially depart from containers of the past so that the users thereof readily understand the procedures necessary to re-cap the needle and which cause the natural instincts of the user to keep his extremities behind the point of the used needle.

These and other objectives of the invention can be more fully understood from the following detailed description and the accompanying drawings in which:

BRIEF DESCRIPTION OF THE DRAWINGS

FIG. 1 is a side view of an assembled needle cartridge,

FIG. 2 is a side view of FIG. 1, partly in section;

FIG. 3 is a side view of FIG. 1, partly in section, in which the cap has been removed from the needle container;

DETAILED DESCRIPTION OF THE DRAWINGS

Figure 4:
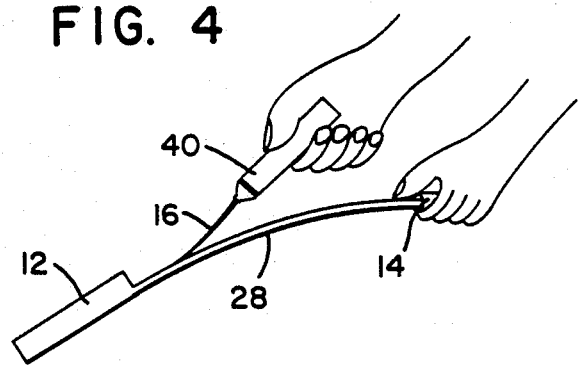
FIG. 4 is an exaggerated, diagrammatic view showing the means by which the syringe needle is re-inserted into its casing with both hands rearwardly of the casing.

Referring now to the drawings wherein like parts are indicated by like numerals, the numeral 10 indicates the needle cartridge of this invention. The principal elements of the cartridge are a casing or container 12 that is enclosed by a cap 14 having a cavity 17. Needle assemblies 15, of the type marketed in such cartridges have a needle 16 extending from a bowl-shaped hub 18. The bowl is open-ended and has an annular lip 20 extending about the bowl opening. Interiorally, the bowl is threaded at 21 to receive a mating exterior thread 39 on the end of a hypodermic syringe 40. The needle 16 has a stem or hollow tube portion 22 extending through the bowl and is sufficiently long to enter the interior of the syringe when threads 21 and 39 are threaded to one another. The tube 22 enters the syringe reservoir in the conventional manner.

Cap 14 is enclosed by end piece 24. The body of the cap is formed with an arcuate aperture 26 formed therein. The casing 12 is formed with an outwardly extending extension arm 28 which is received by the aperture 26 and is terminated by a grasping section or stop 30 the configuration of which does not permit the cap to slip off the extension 28. The cap 14 is freely slidable along the extension from a position frictionally or otherwise secured to casing 12 to the position shown in FIG. 3. Thus, the cap is always connected in one fashion or the other to casing 12.

Throughout its length, the extension 28 is accurately formed at 32 so that the needle 16 is readily guided and returned into the chamber 34 of casing 12 as seen in FIG. 4. The extension 28 is hard plastic, concave and smooth. This facilitates the return of the needle into the casing.

In operation, the container 10 is grasped by the user and the cap 14 is moved to the open or uncovered a position adjacent the stop 30 as seen in FIG. 3. The needle assembly 16 and hub are exposed as the cap 14 is moved to position shown in FIG. 3. The syringe 40 is threaded into bowl 18. After the two are secured, the needle assembly is removed by pulling back on syringe 40.

Figure 5:
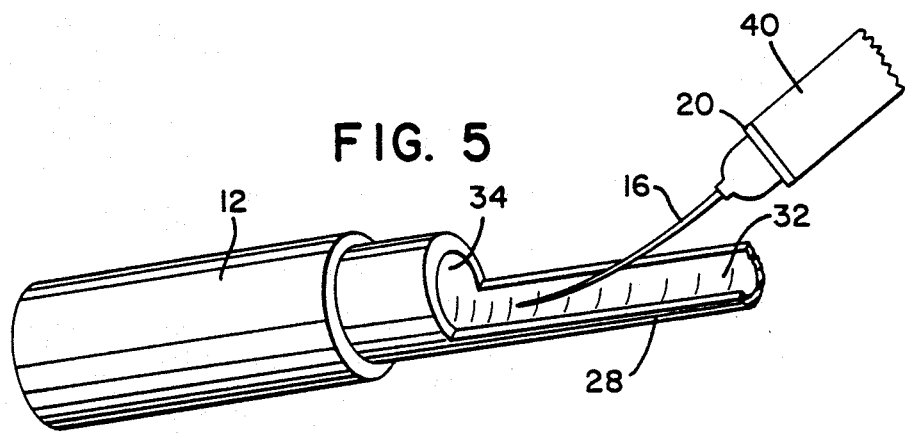
FIG. 5 is an enlarged perspective view of a portion of FIG. 4 showing the configuration of the extension.
Figure 6:
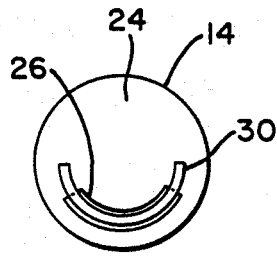
FIG. 6 is an end view along the line 6—6 of FIG. 3.
Figure 7:
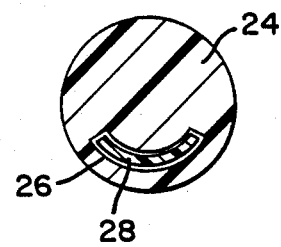
FIG. 7 is a cross-sectional view along the line 7—7 of FIG. 2.
Figure 8:
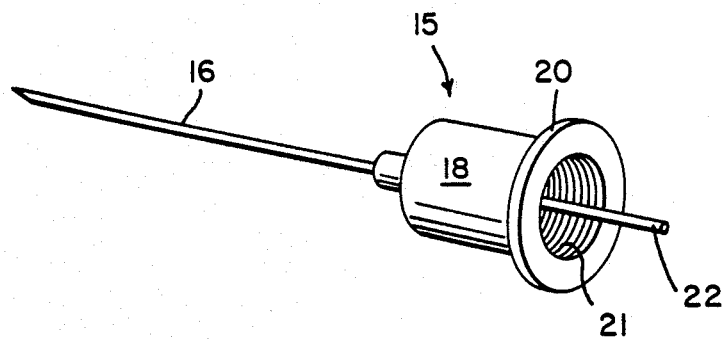
FIG. 8 is a perspective view of the needle assembly.
Figure 9:
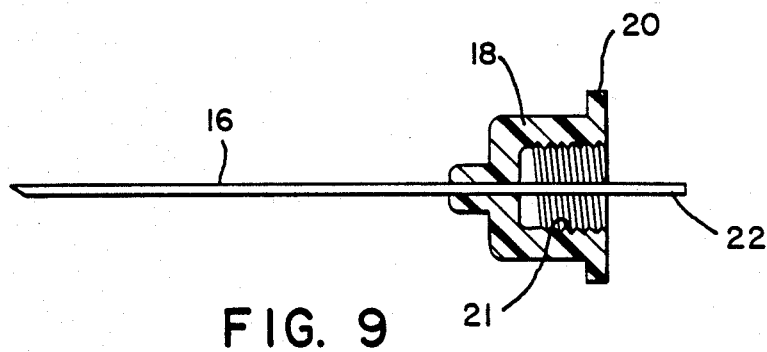
FIG. 9 is a longitudinal cross-section of the needle assembly.
Figure 10:
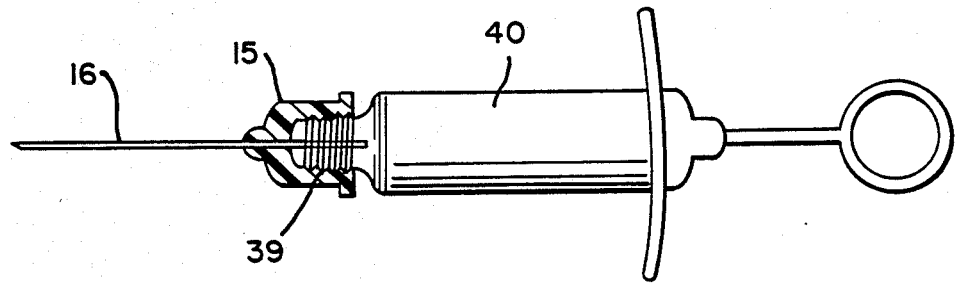
FIG. 10 is a side view of the assembled syringe and needle assembly.

After use, it is desirable and, in some instances, mandatory that the needle be re-capped. As seen in FIG. 4, the user grasps section 30 with one hand and directs the needle 16 into chamber 34 with the other hand. When the needle 16 is returned to casing 12, it is disconnected from the syringe 40 by unscrewing and the cover 14 is moved back to the position shown in FIGS. 1 and 2. The cartridge can then be safely discarded. As seen in FIG. 5, the arcuate surface 32 aids in guiding the needle into position.

Note that the casing 12 is supported by the extension 28. This permits both hands of the user to be rearwardly of the needle point as cap 14 is re-secured. A needle container has been described which is of approximately the same size and cost as containers currently in use. However, the container will eliminate or, at least, greatly reduce the danger of a skin puncture.

In a general manner, while there has been disclosed a preferred embodiment of the invention, it should be understood that the invention is not limited to such an embodiment as there may be changes made in the arrangement, disposition and location of the parts without departing from the principle of the present invention as comprehended within the scope of the accompanying claims.

I claim:
1. A cartridge for housing a syringe needle comprising,
  a casing having a generally cylindrical side wall forming a chamber for receiving said needle and having an open end leading into said chamber,
  a cap having a cylindrical surface and a channel formed in said surface,
  an arm extending outwardly from said side wall and extending through said channel whereby said cap is slidably received on said extension,
  a section formed at the distal end of said extension for grasping same and having a cross-section dimension greater than said channel.
2. The cartridge of claim 1 wherein said casing and said cap are plastic.
3. The cartridge of claim 2 wherein said arm is integral with said casing.
4. The cartridge of claim 3 wherein said arm is arcuate throughout its length and said channel is an arcuate opening snugly receiving said arm.

* * * * *